United States Patent
Gerlach et al.

(10) Patent No.: US 8,650,040 B2
(45) Date of Patent: Feb. 11, 2014

(54) METHOD AND APPARATUS FOR PROTECTING RELATIONSHIPS WITH REFERRING PROVIDERS WITHIN A SYSTEM THAT IDENTIFIES PATIENTS OVERDUE FOR AN APPOINTMENT

(75) Inventors: Brett Cornell Gerlach, Eagle Mountain, UT (US); William Brian Perrin, American Fork, UT (US)

(73) Assignee: Brevium, Inc., Eagle Mountain, UT (US)

( * ) Notice: Subject to any disclaimer, the term of this patent is extended or adjusted under 35 U.S.C. 154(b) by 456 days.

(21) Appl. No.: 12/780,843

(22) Filed: May 14, 2010

(65) Prior Publication Data

US 2011/0282681 A1 Nov. 17, 2011

(51) Int. Cl.
*G06Q 50/00* (2012.01)

(52) U.S. Cl.
USPC .......................................................... 705/2

(58) Field of Classification Search
USPC ...................................................... 705/2, 3
See application file for complete search history.

(56) References Cited

U.S. PATENT DOCUMENTS

| | | |
|---|---|---|
| 5,065,315 A | 11/1991 | Garcia |
| 5,483,443 A | 1/1996 | Milstein et al. |
| 5,557,514 A | 9/1996 | Seare et al. |
| 5,737,726 A | 4/1998 | Cameron et al. |
| 5,748,907 A | 5/1998 | Crane |
| 5,918,208 A | 6/1999 | Javitt |
| 5,982,863 A | 11/1999 | Smiley et al. |
| 6,024,699 A | 2/2000 | Surwit et al. |
| 6,088,429 A | 7/2000 | Garcia |
| 6,151,581 A | 11/2000 | Kraftson et al. |
| 6,223,164 B1 | 4/2001 | Seare et al. |
| 6,393,404 B2 | 5/2002 | Waters et al. |
| 6,680,999 B1 | 1/2004 | Garcia |
| 6,988,075 B1 | 1/2006 | Hacker |
| 7,034,691 B1 | 4/2006 | Rapaport et al. |
| 7,436,311 B2 | 10/2008 | Rapaport et al. |
| 7,702,522 B1 | 4/2010 | Sholem |
| 7,716,072 B1 * | 5/2010 | Green et al. ...................... 705/3 |
| 7,729,928 B2 * | 6/2010 | Backhaus et al. ................. 705/2 |
| 7,774,210 B1 | 8/2010 | Sandberg |
| 7,895,061 B2 * | 2/2011 | Schoenberg ...................... 705/3 |
| 7,916,014 B2 | 3/2011 | Rapaport et al. |
| 7,945,456 B2 * | 5/2011 | Schoenberg ...................... 705/2 |
| 7,970,634 B2 | 6/2011 | Backhaus et al. |
| 8,000,979 B2 | 8/2011 | Blom |
| 8,000,984 B2 | 8/2011 | Hasan et al. |
| 8,090,593 B2 | 1/2012 | Backhaus et al. |

(Continued)

OTHER PUBLICATIONS elexity.com, Webpages, 2004-2007, Exact publication date unknown, Retrieved Jun. 9, 2009, [www.elexity.com; http://web.archive.org/web/20070920075315/www.elexity.com/generalSite/solutionsApptReminders.asp]. 2 Pages.

(Continued)

*Primary Examiner* — Gerald J. O'Connor
*Assistant Examiner* — Edward Winston, III
(74) *Attorney, Agent, or Firm* — Scheinberg & Associates, PC; John B. Kelly; Michael O. Scheinberg (57) ABSTRACT

A method and apparatus for protecting relationships with referring providers, so that when a patient reactivation system is used, patients referred by protected providers will be contacted and invited to make an appointment only when appropriate.

20 Claims, 4 Drawing Sheets

(56) References Cited

U.S. PATENT DOCUMENTS

| | | | |
|---|---|---|---|
| 8,185,426 B1* | 5/2012 | Khoubyari | 705/7.19 |
| 2002/0138306 A1* | 9/2002 | Sabovich | 705/3 |
| 2002/0156672 A1 | 10/2002 | Burko | |
| 2002/0191035 A1 | 12/2002 | Selent | |
| 2003/0120512 A1 | 6/2003 | Dengler | |
| 2003/0179223 A1 | 9/2003 | Ying et al. | |
| 2003/0195774 A1 | 10/2003 | Abbo | |
| 2004/0019501 A1 | 1/2004 | White et al. | |
| 2004/0181433 A1* | 9/2004 | Blair | 705/2 |
| 2004/0199406 A1 | 10/2004 | Owens et al. | |
| 2004/0243436 A1 | 12/2004 | Rawat et al. | |
| 2005/0234739 A1 | 10/2005 | Schoenberg | |
| 2006/0047552 A1* | 3/2006 | Larsen et al. | 705/8 |
| 2006/0047553 A1 | 3/2006 | Fuhrmann et al. | |
| 2006/0047554 A1 | 3/2006 | Larsen et al. | |
| 2006/0053044 A1 | 3/2006 | Kurian et al. | |
| 2007/0078697 A1 | 4/2007 | Nixon | |
| 2008/0306781 A1 | 12/2008 | Gerlach et al. | |
| 2009/0055220 A1 | 2/2009 | Rapaport et al. | |
| 2009/0094054 A1 | 4/2009 | Perrin et al. | |
| 2009/0161846 A1 | 6/2009 | Perrin et al. | |
| 2009/0198509 A1 | 8/2009 | Dumoff | |

OTHER PUBLICATIONS phytel.com, Webpages, 2004, Exact publication date unknown, Retrieved Jun. 9, 2009, [www.phytel.com; http://web.archive.org/web/20041021033228/phytel.com/solutions/appointmentconfirmations.html], 4 Pages.

smilereminder.com, Webpages, 2002, Exact publication date unknown, Retrieved Sep. 17, 2009, [http://web.archive.org/web/20021210135102/www.smilereminder.com/index.html], 3 Pages.

phytel.com, Brochure, 2002, Exact publication date unknown, Retrieved Sep. 17, 2009, [http://web.archive.org/web/20030407162143/phytel.com/brochure.pdf], 6 Pages.

phytel.com, Webpages, 2006, Exact publication date unknown, Retrieved Sep. 17, 2009, [http://web.archive.org/web/20060813164142/http://www.phytel.com], 4 Pages.

phytel.com, Webpages, 2007, Exact publication date unknown, Retrieved Sep. 17, 2009, [http://web.archive. org/web/20071024121500/www.phytel.com/products/products01.htm], 3 Pages.

Corey, David J., "Appointment Standardization Integrated Program Team Meeting—Activation of MCP Status." Department of Defense—Tricare Management Activity, Oct. 24, 2000, 22 Pages.

Health Systems Management Group, "Medical Practice Expert Software Features," Webpages, 2005, Exact publication date unknown, Retrieved Apr. 26, 2010, [http//web.archive.org/web/20050324141543/www.hsmg.biz/cal.med/features/html], 9 Pages.

CPM Marketing Group, Inc., "Life Connections," Webpages, 2006, Exact publication date unknown, Retrieved Apr. 26, 2010, [http://web.archive.org/web/20060308193454/www.cpm.com/physicians/solutions/corecomm.cfm], 8 Pages.

Frieden, Joyce, "Electronic Health Records Yield Business Payoff," Internal Medicine News, Jan. 15, 2006, p. 76, vol. 39, No. 2, p. 76, ISSN 1097-8690, pp. 10-11.

telapatient.com, "PowerCalls—DDS Appointment Confirmation System," Webpages, 1985, Exact publication date unknown, Retrieved Nov. 19, 2009, [http:/www.telapatient.com/pcalls.html], 5 pages.

American Academy of Pediatrics, "Vaccine Reminder Recall System: A Practical Guide for Pediatric Practices," Webpages, Jun. 1984, Timeline for Implementation, Aug. 1989 Complete Electronic Medical Record, [http://practice.aap.org], 5 pages.

ESBSCOHost_Print Search History 01052012.

Hashim, Muhammd Jawad, et al., "Effectiveness of Telephone Reminders in Improving Rate of Appointments Kept at an Outpatient Clinic: A Randomized Controlled Trial." Department of Family Medicine, University of Rochester New York, Mar. 14, 2001.

Mohr, Angie. "Statistics can point you in the direction of profitability." The Record (Kitchener-Waterloo, Ontario), May 4, 2005.

O'Hare, C. Dennis, et al., "The Outcomes of Open-Access Scheduling." Family Practice Management, Feb. 2004, <www.aafp.org/fpm/2004/0200/p35.html>.

ProQuest Search 01052012.

Yedehalli Venkataramu, Raghunandan. "A revenue management framework for appointment allocation in rehabilitation outpatient clinics," Dec. 2005, Wichita State University.

11484340-381857 EICSEARCH.

Adams, Vicki J., et al., 'Analysis of a Practice Management Computer Software Program for Owner Compliance with Recall Reminders,' Can Vet J, Mar. 2006, pp. 234-240, vol. 47.

* cited by examiner

METHOD AND APPARATUS FOR PROTECTING RELATIONSHIPS WITH REFERRING PROVIDERS WITHIN A SYSTEM THAT IDENTIFIES PATIENTS OVERDUE FOR AN APPOINTMENT

TECHNICAL FIELD OF THE INVENTION

The present invention relates to a method and apparatus for internal marketing, and more particularly, to a method and apparatus for identifying and qualifying patients who are due for a health care appointment and facilitating contact with those patients.

BACKGROUND OF THE INVENTION

Using modern data mining techniques based on disease management protocols is a powerful way to identify patients who are overdue for care. With a reliable list of such patients, patients can be efficiently contacted and invited to make an appointment, improving patient care while increasing utilization at, and the financial performance of, the medical practice. However, for practices that receive a large volume of patients by referral, anything that damages trust with referring providers can shut off the flow of referrals and compromise the value of their reactivation program. In cases where patients are referred to specialists and expected to return to the referring provider for routine care after the specialty work is completed, contacting a patient for routine care after treating the patient's referred condition is tantamount to stealing the referred patient, and can destroy trust.

Previous solutions to the referral provider problem have focused on recording and displaying referring provider information. This leads to three problems: First, when contact is handled by an automated system, such as an automated telephone message system or by generating a mailing or email list, this information is simply ignored. Second, when a human is presented with the information, the human may fail to notice that the provider is on a do-not-contact list, and make contact anyway. Third, when multiple referring providers are recorded for a single patient, only one may be displayed, possibly giving preference by referral date or some other criteria without proper heed to protected provider status. With incomplete information displayed, the caller is sure to contact patients belonging to referring providers.

SUMMARY OF THE INVENTION

An object of the present invention is to use healthcare data from a database, and a stored set of preferences, to protect referring provider relationships as part of a patient reactivation system.

The present invention provides a method, system, and computer program product for improving patient reactivation efforts by ensuring that patients who definitely need to return for ongoing care are contacted, while those which should be returned to their referring providers are not contacted.

In a typical embodiment, a system uses information about contacts, patient diagnoses and referring providers, along with preferences regarding which diagnoses or reasons for contact must respect the list of protected referring provider relationships.

The foregoing has outlined rather broadly the features and technical advantages of the present invention in order that the detailed description of the invention that follows may be better understood. The system as described herein includes several inventive aspects, and not all embodiments will include all the features described. Moreover, it should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention and the advantages thereof, reference is now made to the following descriptions taken in conjunction with the accompanying drawings, in which.

DESCRIPTION OF THE PREFERRED EMBODIMENTS

The present invention provides a mechanism for protecting referring provider relationships, so that an effective patient reactivation program can be implemented using modern software tools, while avoiding damage to referring relationships.

For practices that receive a large volume of patients by referral, anything that damages trust with referring providers can shut off the flow of referrals. For example, in cases where patients are referred to specialists and expected to return to the referring provider for routine care after the specialty work is completed, contacting a patient for routine care after treating the patient's referred condition is tantamount to stealing the referred patient, and can destroy trust.

There are, however, situations where it is desirable to contact a patient regardless of referral status. If a doctor indicates that he wants a patient to return for follow-up care, an appointment, or a reactivation notice to later remind the patient to make an appointment, may be entered into the management system. In such cases, that patient can safely be contacted regardless of who referred him. Similarly, there are certain medical conditions that require continuing care from a specialist. Hence, some medical conditions may imply that a patient will stay with the specialist indefinitely, and can therefore be contacted regardless of referring provider.

Embodiments of the present invention provide the healthcare industry with a system that collects medical office preferences about which types of patients can be safely contacted and invited to make an appointment based on the presence of reactivation reasons and patient diagnoses, allows the office to indicate which referring provider relationships should be protected, and then checks all sources of referring provider information and automatically removes patients from the contact list based on these preferences.

Referring provider information is generally stored in one or more of four places in the practice electronic records. It can be found with the patient demographic data, in the appointment data, in the billing data, and/or in electronic medical records data.

When referring provider information is stored per appointment or with the billing data per encounter, it is especially difficult to review manually, because each record must be opened manually and inspected. Machine review of these disparate sources of information is critical for a thorough and efficient qualification of a patient before contract.

Figure 1:
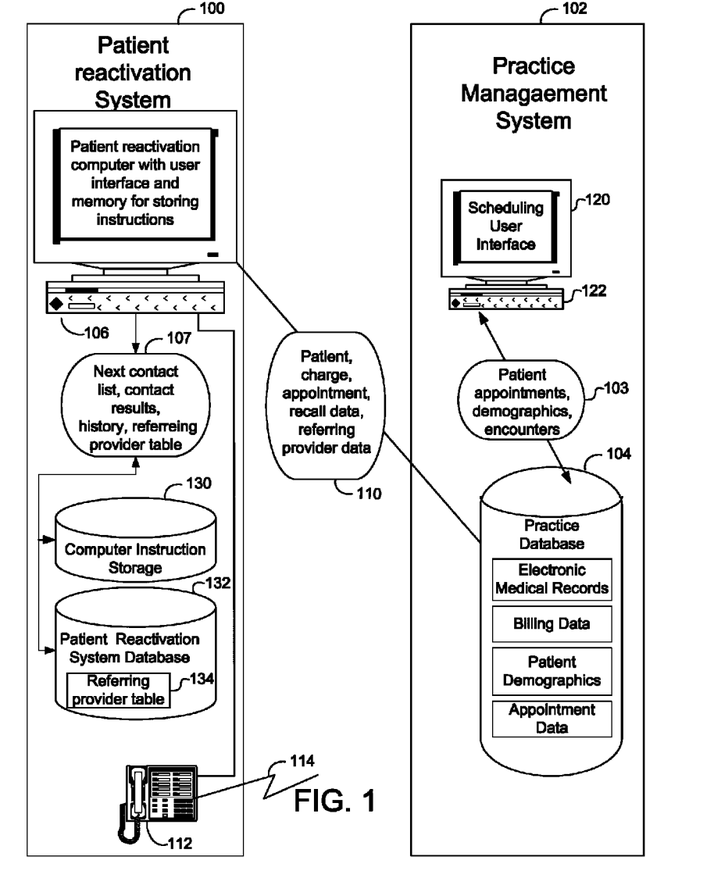
FIG. 1 shows a computer system implementing an embodiment of the present invention.

A preferred embodiment comprises a computer system programmed to carry out specific steps as part of a patient reactivation system software operating on the computer system. FIG. 1 is a block diagram showing the patient reactivation system 100 and an practice management system 102 which can be used together to implement the invention. Patient reactivation system 100 includes a patient reactivation system user computer 106 with a user interface, including, for example, a video display by which a user can view information presented by the system about patients to be called, and a keyboard, mouse, or other device by which the user can enter data into a user computer on the system. In some embodiments, calls to patients may be automated, and made without human assistance. In preferred embodiments, calls are made by a human user in order to better relate to the patients being called. The human user uses a telephone 112 connected to a public telephone network 114 or uses a telephone interface on computer 106. In other embodiments, patients can be contacted by other methods, such as email, either automatically by the computer or by a human user of the system. Patient reactivation system 100 also includes computer instruction storage 130 and patient reactivation system database 132, which includes a referring provider data table 134. Patient reactivation system database 132 stores lists of patients to contact and information about the patients necessary to make the contact. Computer instruction storage 130 stores computer instructions for executing the steps of the present invention. Referring provider database table 134 is described in more detail below. Computer instruction storage 130 and patient reactivation system database 132 may be stored on user computer 106 or on a network storage location. The patient reactivation system 100 interfaces with practice management system 102, which includes a scheduling computer with a scheduling user interface 120 and a management system database 104 that typically includes billing codes. The billing codes can be used to determine when additional visits are required.

Scheduling computer 122 draws patient appointments 103 and other data from the practice database 104, and writes new appointments 103 and other data into the practice database 104. The patient reactivation system 100 determines, as described for example in U.S. patent application Ser. No. 11/938,087 for "Method and Apparatus for Identifying Patients Overdue for an Appointment Using Standard Healthcare Billing Data," which is hereby incorporated by reference, which patients should be contacted 110 and prompts one or more users to contact these patients. The contact results and history 107 are stored into the patient reactivation system database 108. The patient reactivation system 100 queries the patient reactivation system database 108 to avoid contacting patients redundantly or too frequently. The referring provider table stores information about referring providers and whether each is protected, as well as conditions that permit contacting patients of protected providers. The referring provider table 134 is queried when generating a call list to protect relationships with protected providers.

Figure 2:
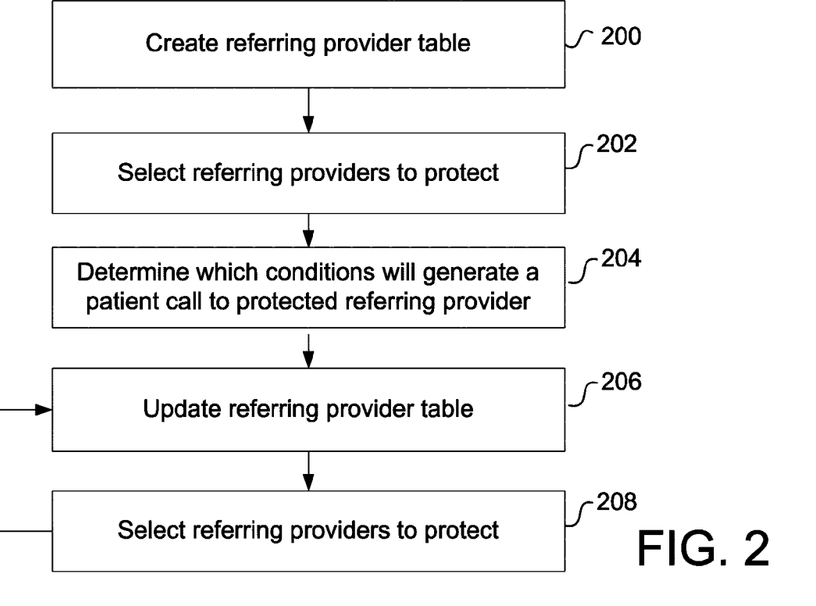
FIG. 2 is a flowchart showing steps of a preferred embodiment of the present invention.
Figure 3:
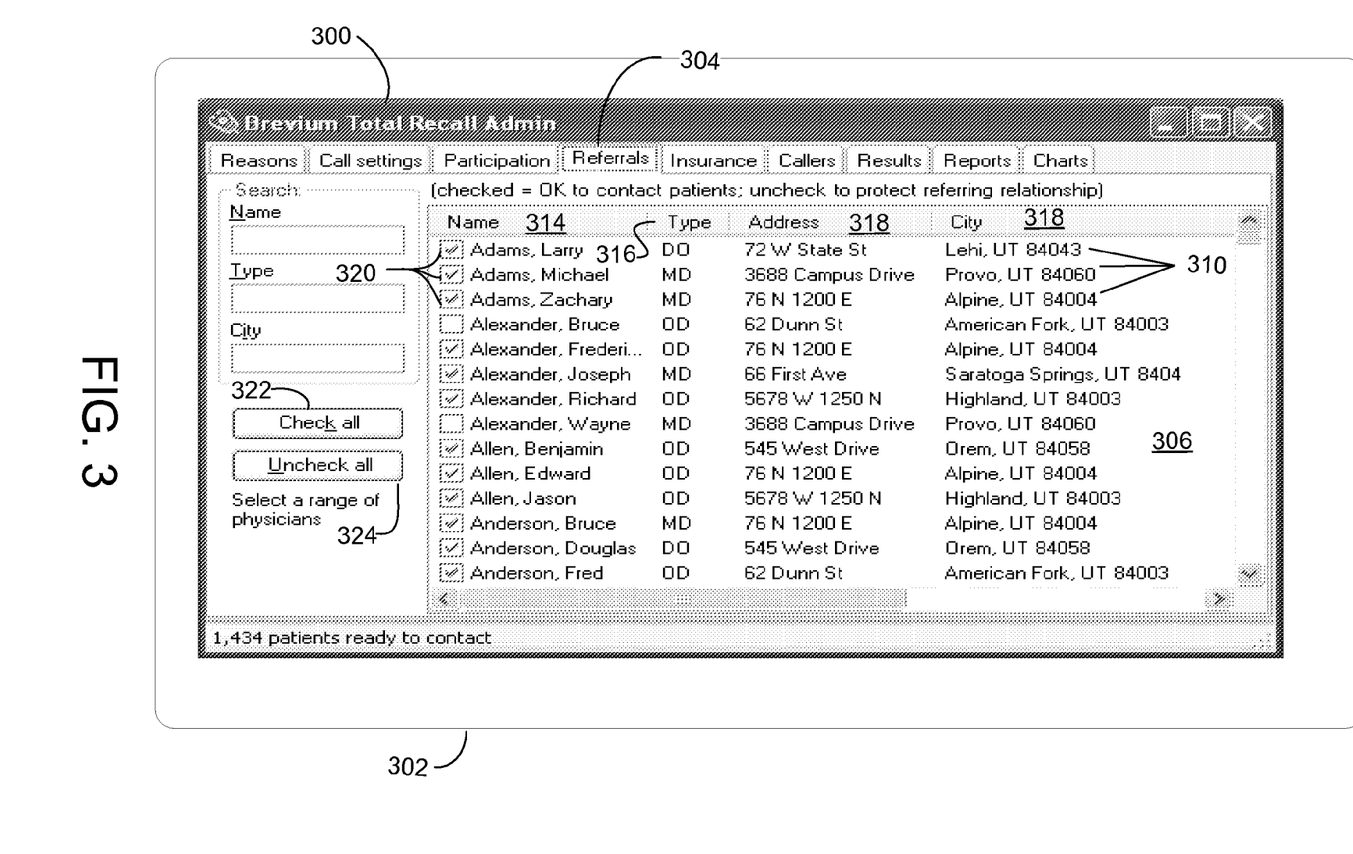
FIG. 3 shows the Referrals tab, which enables the medical office to designate which referring providers should be protected. Bruce Alexander and Wayne Alexander are marked as protected.

FIG. 2 is a flow chart showing preferred steps for setting up a system of the present invention. In step 200, a referring provider table is created, if it does not already exist. The referring provider table is typically incorporated into the patient reactivation system database and includes all referring providers listed in patient records. FIG. 3 shows an example of a window 300 displayed on a computer screen 302 in which a patient reactivation system is operating. Under the referral tab 304 is a view 306 of the referring provider database table 134 that allows a user to review referring provider information. The database includes a record 310 for each referring provider, and each record includes a field for the provider name 314, type of provider 316, and contact information 318, such as address and/or phone number. Type of referring provider may include, for example, medical doctor (MD), doctor of osteopathy (DO), doctor of optometry (OD), or other types of providers.

On the initial set-up of the referring provider database in step 200, the software searches patient demographic data, appointment data, billing data, and/or in electronic medical records data in practice management database or databases to locate referring providers, and lists any referring providers found in the referring provider table of the patient reactivation system database. Step 200 can be performed manually, with a person reviewing the patient records to locate referring provider information; automatically without human intervention, with software locating provider information from various places in the patient record, or some combination of computer and human actions.

All referring providers are listed with identifying information and a checkbox to indicate whether to "safely ignore" or "protect" a referring relationship. The checkbox 320 is included as part of the provider name field and indicates whether or not it is necessary to consider the relationship with the referring provider when determining whether to contact the patient for additional appointments. If the box is checked, the referring provider is not protected, and the patient will be contacted whenever indicated by the reactivation system, without regard to the referring provider. In step 202, the practice would uncheck any providers that it wants to protect. The computer user can check or uncheck check boxes 320 for individual referring providers, can check all providers using button 322, uncheck all providers using button 324, or can select a range of providers to protect or unprotect.

If a provider is checked, his referred patients will always be called. If unchecked, then only those patients with conditions indicating it is safe to contact, as described in more detail below, will be contacted.

Figure 4:
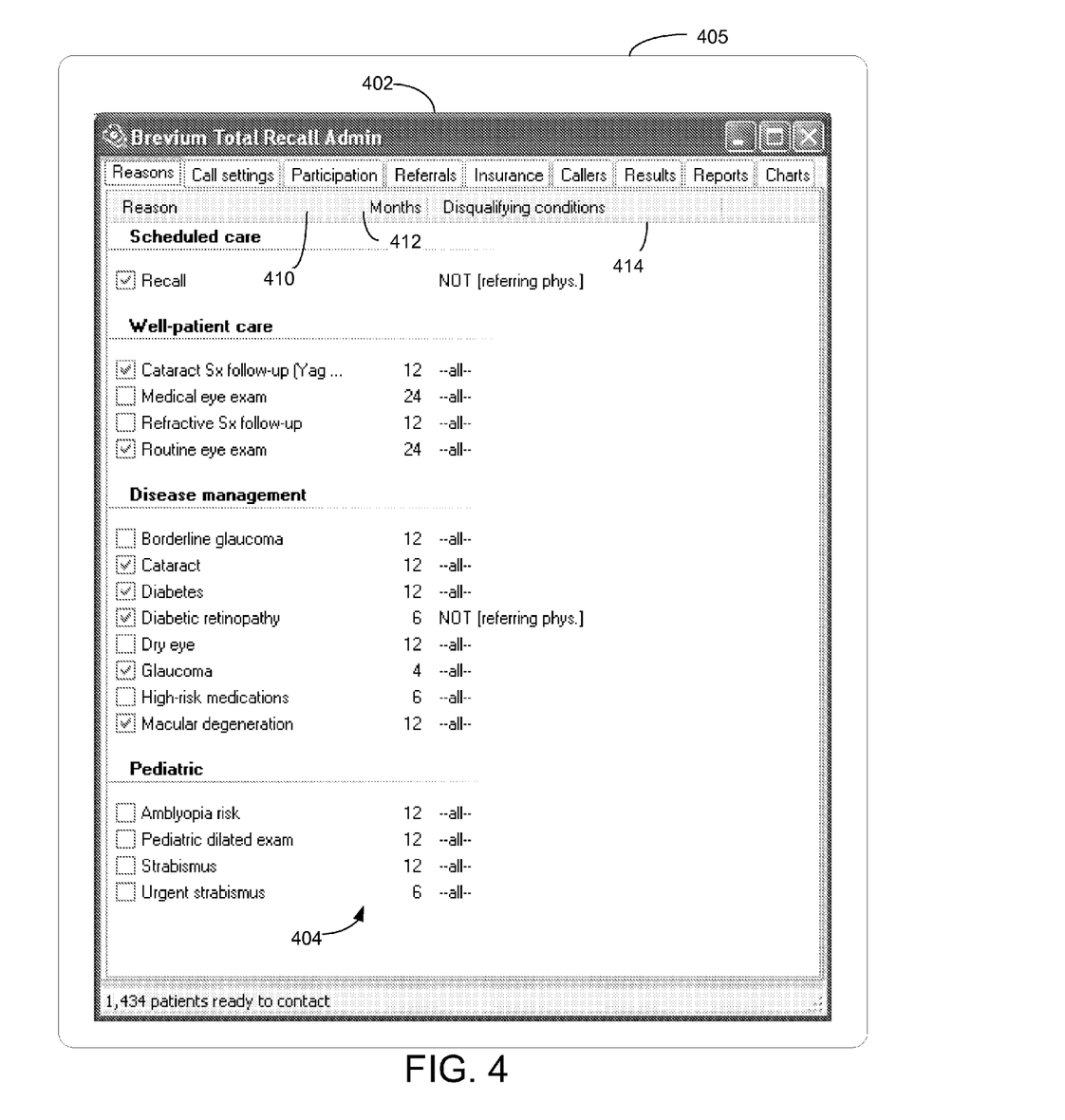
FIG. 4 shows the Reasons tab, which allows the medical office to indicate when to respect or ignore the protected referring provider designations recorded in the referrals tab, based on the reason for contact.

In step 204, the practice indicates which conditions will not prevent contact with patients of protected providers, that is, which conditions are an exception to the default of disqualifying or not contacting patients of protected providers. FIG. 4 shows a window 402 on a computer screen 405 displaying a table 404 of reactivation software. Table 404 displays reasons for contact in column 410, visit intervals in column 412, and disqualifying conditions in column 414. The reasons column 410 includes check boxes that, when checked, indicates that a patient with the specified condition will be contacted at the time indicated in column 412, unless a disqualifying condition is met. Disqualifying conditions can include, for example, a patient that has changed physicians. In accordance with the invention, one of the disqualifying conditions is a protected referring provider. When the "disqualifying conditions" column 414 indicates "all," then any disqualifying reason, including a protected referring provider, will prevent the system from contacting the patient. The default is typically set so that a protected referring provider will prevent contact. When the "disqualifying conditions" indicate "NOT [referring phys.]" then a protected referring provider will not prevent contact.

As shown in FIG. 4, a practice can set or unset conditions that permit or disqualify a patient contact. For example, FIG. 4 shows that a patient having diabetic retinopathy will not be disqualified from contact because of a protected referring provider. Once these preferences are recorded, they are used within the data mining queries to determine whether a patient should or should not be included in the contact list. The setting of disqualifying conditions is typically done "per practice," that is, the settings apply to all referring providers in the practice database, although individual setting for each provider could be used in some embodiments.

The referring provider database is updated regularly in step 206, for example, each evening or whenever new information is added to one of the data sources, to add records to incorporate new referring providers. The practice can be presented with the choice of whether a newly added referring provider is to be protected again in step 208 whenever a new referring provider is added to the database.

Figure 5:
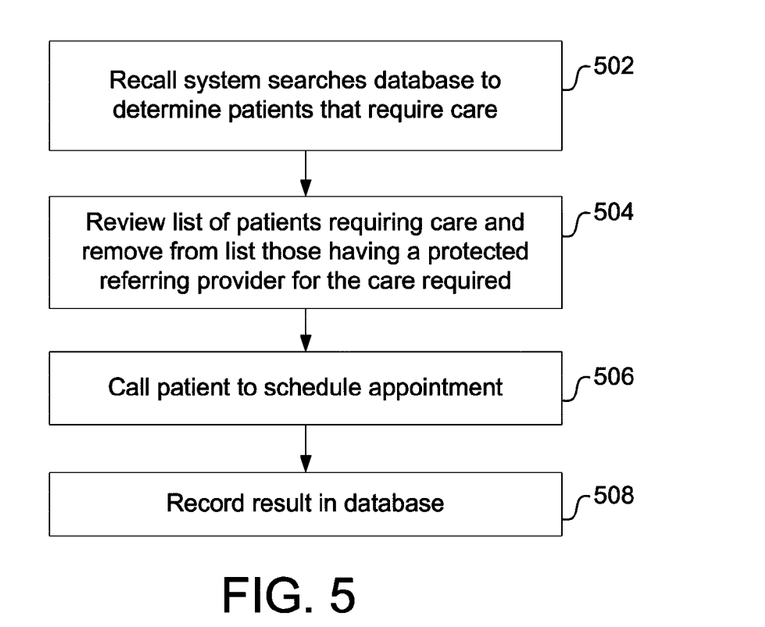
FIG. 5 is a flow chart showing the steps of a patient reactivation system.

FIG. 5 shows the steps involved in operation of a preferred embodiment. In step 502, the reactivation system examines the reactivation database to find patients that require care within a specific period of time. The reactivation database may be compiled as described in U.S. patent application Ser. No. 11/938,087 for "Method and Apparatus for Identifying Patients Overdue for an Appointment Using Standard Healthcare Billing Data." In step 504, the software reviews the list of patients requiring care and eliminates those patients that are disqualified from receiving a call. One disqualifying reason is that the referring provided is protected for the care required. In some embodiments, a list of potential patients to call is compiled, and then the list is culled to remove patients having a disqualifying factor, such as a protected referring provider. In other embodiments, patients to be contacted are checked for disqualifying factors before being placed on the list. In some embodiments, patients having a protected referring provider are listed in the contact list presented to the caller, along with an indication that the patient has a protected referring provider. The indication may be, for example, simply listing the name of the provider and/or an explicit notice or warning that the patient has a protected referring provider. In step 506, a human user telephones the patients that require care and that are not eliminated from the call list or subject to an indication of a protected referring provider, and schedules an appointment. Alternatively, a computer generated call could be placed. In step 508, the results of the call, such as, appointment scheduled, no answer, wrong number, are recorded in the reactivation database.

Patients often have more than one reason for contact. When a patient matches at least one reason with a preference indicating that the referring provider designation should be ignored, then the designation shall be ignored. For example, if a patient has an ignored contact card and has diabetes, hence matching two reasons for contact, and the contact card is marked as ignore the referring provider, whereas the diabetes rule says to respect the referring provider designation, then the referring provider designation shall be ignored, and the patient placed on the contact list regardless of who referred that patient.

Because many practice management systems allow referring provider information to be recorded in multiple places, and allow each appointment and encounter to have its own referring provider, a patient may have more than one referring provider. In this case, if the referring provider designation is to be respected based on the above logic, and if any of the referring providers is designated to be protected, then the patient shall not be placed on the contact list.

If the system indicates that an unsuccessful attempt was made to contact a patient, that is, the patient is already in the reactivation system, the system will ignore information about a protected referring provider when making further attempts to contact the patient.

The invention also includes computer readable media, such as optical or magnetic media, having stored thereon computer instruction for executing steps of the invention. The term "user" or "practice" when describing a person performing steps indicates a person working on behalf of a health care practice. It should be understood that various changes, substitutions and alterations could be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A computer-implemented system for improving health care provider practices by considering referral information in the generation of a contact list, the computer-implemented system comprising:
   one or more computers executing computer instructions for automatically performing the steps of:
      examining a patient reactivation database of a first health care provider;
      identifying patients in the patient reactivation database who require health care within a specified period of time but who do not have an appointment scheduled with the first health care provider;
      generating a contact list, the contact list comprising a list of the patients who require health care within a specified period of time but who do not have an appointment scheduled with the first health care provider;
      comparing patients in contact list with a list of referring providers, each referring provider comprising a second health care provider that previously referred one or more patients to the first health care provider, at least some of the referring providers being protected referring providers; and
      removing from the contact list those patients who were referred to the first health care provider by a protected referring provider or indicating in the contact list those patients who were referred to the first health care provider by protected referring providers.

2. The computer-implemented system of claim 1 further comprising, subsequent to the removing or indicating step, contacting the patients on the contact list who were not referred by a protected referring provider to schedule health care appointments.

3. The computer-implemented system of claim 2 in which contacting patients on the contact list includes contacting the patients by telephone or email.

4. The computer-implemented system of claim 1 in which providing an indication in the contact list includes providing to a caller an explicit notice or warning that a patient in the contact list has a protected referring provider.

5. The computer-implemented system of claim 1 in which a patient that was set up for a recall notice in the practice management system or electronic medical record system will not be excluded from or indicated in the contact list, regardless of whether the referring provider is a protected referring provider.

6. The computer-implemented system of claim 1 further comprising:
one or more computers executing computer instructions for automatically performing the steps of:
searching by a computer executing computer instructions a health care practice database to identify referring providers; and
generating by a computer executing computer instructions a list of the referring providers.

7. The computer-implemented system of claim 6 in which searching by a computer executing computer instructions a health care practice database to identify referring providers includes searching one or more of patient demographic data, appointment data, billing data, and electronic medical records data.

8. The computer-implemented system of claim 6 further comprising analyzing multiple sources of referring provider information, and excluding from or indicating in the contact list, patients having one or more protected referring providers, thereby protecting referring providers by using the multiple sources of information.

9. The computer-implemented system of claim 6 further comprising analyzing multiple sources of referring provider information, and displaying the names of one or more protected providers, displaying a warning, or displaying both the name of the one or more protected providers and a warning, when prompting a user to contact patients with one or more referring providers to protect referring providers across these sources.

10. The computer-implemented system of claim 6 further comprising indicating on a list of reasons for contact whether the existence of a protected referring provider will prevent the contact.

11. The computer-implemented system of claim 10 in which excluding from the patients to be called those that were referred by referring providers having protected status includes failing to exclude at least one patient having a contact reason that is indicated in the computer memory as requiring a contact regardless of whether the referring provider is a protected referring provider.

12. The computer-implemented system of claim 10 in which if a patient has multiple reasons for contact and at least one reason indicates that the patient should be contacted even if the referring provider is indicated as a protected referring provider, then the patient is placed on the contact list and not indicated.

13. The computer-implemented system of claim 10 in which a patient has multiple referring providers and in which if any of the multiple referring providers is protected, the patient is not contacted unless at least one reason indicates that the patient should be called even if the referring provider is indicated as a protected referring provider.

14. The computer-implemented system of claim 10 in which excluding from or indicating the contact list patients that were referred by protected referring providers includes verifying that the reason for the contact does not provide an exception from protected status that allows a contact before eliminating patients from the contact list.

15. A computer programmed to execute the steps of:
examining a patient reactivation database of a first health care provider;
identifying patients in the patient reactivation database who require health care within a specified period of time but who do not have an appointment scheduled with the first health care provider;
generating a contact list, the contact list comprising a list of the patients who require health care within a specified period of time but who do not have an appointment scheduled with the first health care provider;
comparing patients in the contact list with a list of referring providers, each referring provider comprising a second health care provider that previously referred one or more patients to the first health care provider, at least some of the referring providers being protected referring providers; and
removing from the contact list those patients who were referred to the first health care provider by a protected referring provider or indicating in the contact list those patients who were referred to the first health care provider by protected referring providers.

16. A nontransitory computer readable media encoded with computer instructions for executing the steps of:
examining a patient reactivation database of a first health care provider;
identifying patients in the patient reactivation database who require health care within a specified period of time but who do not have an appointment scheduled with the first health care provider;
generating by a computer executing the computer instructions a contact list, the contact list comprising a list of the patients who require health care within a specified period of time but who do not have an appointment scheduled with the first health care provider;
comparing by a computer executing the computer instructions patients in the contact list with a list of referring providers, each referring provider comprising a second health care provider that previously referred one or more patients to the first health care provider, at least some of the referring providers being protected referring providers; and
removing from the contact list those patients that were referred to the first health care provider by protected referring providers or indicating in the contact list those patients who were referred to the first health care provider by protected referring providers.

17. A computer-implemented method for improving health care provider practices by considering referral information in the generation of contact list, comprising:
examining a patient reactivation database of a first health care provider;
identifying patients in the patient reactivation database who require health care within a specified period of time but who do not have an appointment scheduled with the first health care provider;
generating by a computer executing computer instructions a contact list, the contact list comprising a list of the patients who require health care within a specified period of time but who do not have an appointment scheduled with the first health care provider;
comparing by a computer executing computer instructions patients in the contact list with a list of referring providers, each referring provider comprising a second health care provider that previously referred one or more patients to the first health care provider, at least some of the referring providers having an indication of protected status; and removing from the contact list those patients who were referred to the first health care provider by a protected referring provider or indicating in the contact list those patients who were referred to the first health care provider by protected referring providers.

18. The computer implemented method of claim 17 in which determining based on referring provider information in one or more electronic databases whether the patient should be contacted by the practice to schedule an appointment includes determining based on referring provider information and on the reason for the appointment whether the patient should be contacted by the practice to schedule an appointment.

19. The computer implemented method of claim 17 further comprising compiling by the computer a list of referring providers, the referring providers designated in the list as protected or not protected.

20. The computer implemented method of claim 17 in which reviewing practice records in one or more electronic databases to determine whether a patient requires an appointment includes determining a reason a patient requires the appointment and further comprising determining from the computer memory whether a protected provider is a disqualifying condition for the determined reason.

* * * * *